(12) United States Patent
Bagaoisan et al.

(10) Patent No.: US 7,806,856 B2
(45) Date of Patent: Oct. 5, 2010

(54) APPARATUS AND METHOD FOR TEMPORARY HEMOSTASIS

(75) Inventors: Celso J. Bagaoisan, Union City, CA (US); Jefferey Bleam, Boulder Creek, CA (US); Roy Leguidleguid, Union City, CA (US)

(73) Assignee: AccessClosure, Inc., Mountain View, CA (US)

( * ) Notice: Subject to any disclaimer, the term of this patent is extended or adjusted under 35 U.S.C. 154(b) by 687 days.

(21) Appl. No.: 11/112,971

(22) Filed: Apr. 22, 2005

(65) Prior Publication Data

US 2008/0009794 A1    Jan. 10, 2008

(51) Int. Cl.
*A61M 29/00* (2006.01)
*A61M 31/00* (2006.01)
*A61M 37/00* (2006.01)

(52) U.S. Cl. ............. 604/97.03; 604/99.03; 604/103.03
(58) Field of Classification Search ... 604/97.01–99.04, 604/103.03, 104–108, 544
See application file for complete search history.

(56) References Cited

U.S. PATENT DOCUMENTS

| | | | | |
|---|---|---|---|---|
| 827,193 | A * | 7/1906 | Thrash | ......... 604/105 |
| 2,365,039 | A | 12/1944 | Andresen | |
| 3,731,691 | A * | 5/1973 | Chen | ......... 128/207.15 |
| 3,765,419 | A | 10/1973 | Usher | |
| 4,002,173 | A | 1/1977 | Manning | |
| 4,271,839 | A * | 6/1981 | Fogarty et al. | ......... 606/194 |
| 4,403,988 | A * | 9/1983 | Binard et al. | ......... 604/118 |
| 4,439,185 | A * | 3/1984 | Lundquist | ......... 604/97.02 |
| 4,472,542 | A | 9/1984 | Nambu | |
| 4,598,707 | A | 7/1986 | Agdanowski et al. | |
| 4,655,211 | A | 4/1987 | Sakamoto | |
| 4,664,857 | A | 5/1987 | Nambu | |
| 4,734,097 | A | 3/1988 | Tanabe | |
| 4,738,658 | A | 4/1988 | Magro | |
| 4,801,293 | A * | 1/1989 | Jackson | ......... 604/505 |
| 4,838,280 | A | 6/1989 | Haaga | |
| 4,852,568 | A | 8/1989 | Kensey | |

(Continued)

FOREIGN PATENT DOCUMENTS

| | | |
|---|---|---|
| WO | 9222252 | 12/1992 |
| WO | WO 92/22252 | 12/1992 |
| WO | 9533510 | 12/1995 |
| WO | 0014155 | 3/2000 |
| WO | 0019912 | 4/2000 |

(Continued)

OTHER PUBLICATIONS

PCT International Search Report for PCT/US2006/014562, Applicant: AccessClosure, Inc., Forms PCT/ISA/210 and PCT/ISA/220, dated Aug. 12, 2006, 8 pages.

(Continued)

*Primary Examiner*—Nicholas D Lucchesi
*Assistant Examiner*—Nathan R Price
(74) *Attorney, Agent, or Firm*—William A. English; Vista IP Law Group LLP (57) ABSTRACT

An apparatus for providing hemostasis within a puncture through tissue includes an elongate member having a lumen extending between proximal and distal ends thereof, an expandable member carried on the distal end and a housing on the proximal end, the housing including an interior communicating with the lumen, and further including a valve assembly with a one-way valve allowing access into the housing interior upon application of a pressure differential across the valve, and a movable plunger for overriding and opening the valve.

16 Claims, 10 Drawing Sheets

U.S. PATENT DOCUMENTS

| | | | |
|---|---|---|---|
| 4,890,612 A * | 1/1990 | Kensey | 606/213 |
| 4,932,938 A * | 6/1990 | Goldberg et al. | 604/99.04 |
| 4,948,092 A | 8/1990 | Kasper et al. | |
| 5,061,274 A | 10/1991 | Kensey | |
| 5,085,249 A | 2/1992 | Dragan et al. | |
| 5,087,246 A * | 2/1992 | Smith | 604/103.13 |
| 5,108,421 A | 4/1992 | Fowler | |
| 5,192,302 A | 3/1993 | Kensey | |
| 5,221,259 A | 6/1993 | Weldom | |
| 5,222,974 A | 6/1993 | Kensey et al. | |
| 5,258,042 A | 11/1993 | Mehta | |
| 5,290,310 A | 3/1994 | Makower | |
| 5,292,332 A | 3/1994 | Lee | |
| 5,320,639 A | 6/1994 | Rudnick | |
| 5,324,306 A | 6/1994 | Makower | |
| 5,334,216 A | 8/1994 | Vidal | |
| 5,370,660 A | 12/1994 | Weinstein | |
| 5,383,896 A | 1/1995 | Gershony | |
| 5,409,703 A | 4/1995 | McAnalley | |
| 5,413,571 A | 5/1995 | Katsaros | |
| 5,419,765 A | 5/1995 | Weldon | |
| 5,431,639 A | 7/1995 | Shaw | |
| 5,437,292 A | 8/1995 | Kipshidze | |
| 5,437,631 A | 8/1995 | Janzen | |
| 5,441,517 A | 8/1995 | Kensey et al. | |
| 5,464,396 A | 11/1995 | Barta | |
| 5,486,195 A | 1/1996 | Myers | |
| 5,514,158 A | 5/1996 | Kanesaka | |
| 5,529,577 A | 6/1996 | Hammerslag | |
| 5,550,187 A | 8/1996 | Rhee | |
| 5,571,181 A | 11/1996 | Li | |
| 5,580,923 A | 12/1996 | Yeung | |
| 5,626,601 A | 5/1997 | Gershony | |
| 5,643,464 A | 7/1997 | Rhee et al. | |
| 5,700,477 A | 12/1997 | Rosenthal | |
| 5,716,375 A | 2/1998 | Fowler | |
| 5,718,916 A | 2/1998 | Scherr | |
| 5,725,498 A | 3/1998 | Janzen | |
| 5,725,551 A | 3/1998 | Myers | |
| 5,744,153 A | 4/1998 | Yewey | |
| 5,752,974 A | 5/1998 | Rhee | |
| 5,780,044 A | 7/1998 | Yewey | |
| 5,782,860 A | 7/1998 | Epstein | |
| 5,785,679 A | 7/1998 | Abolfathi | |
| 5,814,016 A * | 9/1998 | Valley et al. | 604/96.01 |
| 5,836,970 A | 11/1998 | Pandit | |
| 5,868,778 A | 2/1999 | Gershony | |
| 5,902,273 A * | 5/1999 | Yang et al. | 604/118 |
| 5,916,236 A | 6/1999 | Van de Moer | |
| 5,928,266 A | 7/1999 | Kontos | |
| 5,948,429 A | 9/1999 | Bell | |
| 5,948,829 A | 9/1999 | Wallajapet | |
| 5,951,583 A | 9/1999 | Jensen | |
| 5,957,952 A | 9/1999 | Gershony | |
| 5,972,375 A | 10/1999 | Truter | |
| 5,973,014 A | 10/1999 | Funk | |
| 6,017,359 A | 1/2000 | Gershony | |
| 6,022,361 A | 2/2000 | Epstein | |
| 6,045,570 A | 4/2000 | Epstein | |
| 6,048,358 A | 4/2000 | Barak | |
| 6,051,248 A | 4/2000 | Sawhney | |
| 6,056,768 A | 5/2000 | Cates | |
| 6,056,769 A | 5/2000 | Epstein | |
| 6,083,522 A | 7/2000 | Chu | |
| 6,152,943 A | 11/2000 | Sawhney | |
| 6,162,240 A | 12/2000 | Cates | |
| 6,162,241 A | 12/2000 | Coury | |
| 6,165,201 A | 12/2000 | Sawhney et al. | |
| 6,179,862 B1 | 1/2001 | Sawhney | |
| 6,238,412 B1 | 5/2001 | Dubrul | |
| 6,271,278 B1 | 8/2001 | Park | |
| 6,287,323 B1 | 9/2001 | Hammerslag | |
| 6,296,658 B1 | 10/2001 | Gershony | |
| 6,302,898 B1 | 10/2001 | Edwards | |
| 6,312,407 B1 * | 11/2001 | Zadno-Azizi et al. | 604/103.03 |
| 6,325,789 B1 | 12/2001 | Janzen | |
| 6,350,274 B1 | 2/2002 | Li | |
| 6,371,975 B1 | 4/2002 | Cruise | |
| 6,379,373 B1 | 4/2002 | Sawhney et al. | |
| 6,458,147 B1 | 10/2002 | Cruise | |
| 6,475,177 B1 | 11/2002 | Suzuki | |
| 6,514,534 B1 | 2/2003 | Sawhney | |
| 6,562,059 B2 | 5/2003 | Edwards | |
| 6,566,406 B1 | 5/2003 | Pathak | |
| 6,569,185 B2 | 5/2003 | Ungs | |
| 6,605,294 B2 | 8/2003 | Sawhney | |
| 6,608,117 B1 | 8/2003 | Gvozdic | |
| 6,610,026 B2 | 8/2003 | Cragg | |
| 6,613,070 B2 | 9/2003 | Redmond | |
| 6,626,861 B1 | 9/2003 | Hart | |
| 6,626,918 B1 | 9/2003 | Ginn | |
| 6,635,068 B1 | 10/2003 | Dubrul | |
| 6,689,148 B2 | 2/2004 | Sawhney | |
| 6,703,047 B2 | 3/2004 | Sawhney | |
| 6,774,151 B2 | 8/2004 | Malmgren | |
| 6,818,008 B1 | 11/2004 | Cates | |
| 6,818,018 B1 | 11/2004 | Sawhney | |
| 6,863,924 B2 | 3/2005 | Ranganathan | |
| 6,887,974 B2 | 5/2005 | Pathak | |
| 6,960,617 B2 | 11/2005 | Omididan | |
| 7,335,220 B2 | 2/2008 | Khosravi | |
| 2001/0031948 A1 | 10/2001 | Cruise | |
| 2001/0046518 A1 | 11/2001 | Sawhney | |
| 2001/0047187 A1 | 11/2001 | Milo | |
| 2001/0051813 A1 | 12/2001 | Hnojewyj | |
| 2002/0062104 A1 | 5/2002 | Ashby | |
| 2002/0072767 A1 | 6/2002 | Zhu | |
| 2002/0106409 A1 | 8/2002 | Sawhney | |
| 2002/0114775 A1 | 8/2002 | Pathak | |
| 2002/0188319 A1 | 12/2002 | Morris | |
| 2002/0193808 A1 | 12/2002 | Belef | |
| 2003/0012734 A1 | 1/2003 | Pathak | |
| 2003/0051735 A1 | 3/2003 | Pavcnik | |
| 2004/0122350 A1 | 6/2004 | Zhong | |
| 2004/0249342 A1 | 12/2004 | Khosravi et al. | |
| 2004/0267308 A1 | 12/2004 | Bagaoisan | |
| 2005/0085852 A1 | 4/2005 | Ditter | |
| 2006/0034930 A1 | 2/2006 | Khosravi | |
| 2006/0100664 A1 | 5/2006 | Pai | |
| 2006/0253072 A1 | 11/2006 | Pai | |

FOREIGN PATENT DOCUMENTS

| | | |
|---|---|---|
| WO | WO 00/19912 | 4/2000 |
| WO | 03094749 | 11/2003 |
| WO | WO 03/094749 | 11/2003 |

OTHER PUBLICATIONS

PCT Written Opinion for PCT/US2006/014562, Applicant: AccessClosure, Inc., Forms PCT/ISA/237, dated Aug. 12, 2006, 8 pages.

Office Action on U.S. Appl. No. 10/806,952 dated Jul. 3, 2007, 13 pages.

Response to Office Action for U.S. Appl. No. 10/806,952 dated Nov. 5, 2007, 17 pages.

Office Action on U.S. Appl. No. 10/806,952 dated Apr. 25, 2008, 12 pages.

Response to Office Action for U.S. Appl. No. 10/806,952 dated Jul. 25, 2008, 16 pages.

\* cited by examiner

APPARATUS AND METHOD FOR TEMPORARY HEMOSTASIS

FIELD OF THE INVENTION

The present invention relates generally to apparatus and methods used for sealing a percutaneous puncture extending from a patient's skin to a blood vessel or other body lumen to seal the puncture.

BACKGROUND

Apparatus and methods are known for accessing a patient's vasculature percutaneously, e.g., to perform a procedure within the vasculature, and for sealing the puncture that results after completing the procedure. For example, a hollow needle may be inserted through a patient's skin and overlying tissue into a blood vessel. A guide wire may be passed through the needle lumen into the blood vessel, whereupon the needle may be removed. An introducer sheath may then be advanced over the guide wire into the vessel, e.g., in conjunction with or subsequent to one or more dilators.

A catheter or other device may be advanced through the introducer sheath and over the guide wire into a position for performing a medical procedure. Thus, the introducer sheath may facilitate introducing various devices into the vessel, while minimizing trauma to the vessel wall and/or minimizing blood loss. Upon completing the procedure, the device(s) and introducer sheath may be removed, leaving a puncture extending between the skin and the vessel wall.

To seal the puncture, external pressure may be applied to the overlying tissue, e.g., manually and/or using sandbags, until hemostasis occurs. This procedure, however, may be time consuming and expensive, requiring as much as an hour of a medical professional's time. It is also uncomfortable for the patient, and may require the patient to remain immobilized in the operating room, catheter lab, or holding area. In addition, a risk of hematoma exists from bleeding before hemostasis occurs.

Various apparatus and methods have been suggested for sealing a percutaneous puncture instead of or in addition to using external pressure. For example, U.S. Pat. No. 5,108,421 issued to Fowler, and U.S. Pat. Nos. 5,192,302 and 5,222,974 issued to Kensey et al., describe delivering a collagen plug into a puncture site.

Such sealing methods generally involve introducing plugs or other materials into the puncture after completing the procedure and removing the introducer sheath. With the introducer sheath removed, there is substantial risk of hematoma within the tissue surrounding the puncture as blood from the vessel leaks into the puncture, which may be uncomfortable and/or harmful to the patient. Further, temporary hemostasis devices for isolating the vessel from the puncture may be difficult to use effectively and/or may be expensive. Despite attempts to isolate the vessel from the puncture while delivering a plug or other sealing material, the sealing material may still leak and/or become exposed in the vessel, where the sealing material may risk causing an embolism in the vessel.

SUMMARY OF THE INVENTION

The present invention is directed to apparatus and methods for providing hemostasis. The apparatus and methods may be used to provide temporary or permanent hemostasis, e.g., within a vascular puncture extending into a blood vessel. The apparatus and methods may also be used for delivering a sealing compound or sealing device, such as a liquid polymer or solid plug or carrier, into a percutaneous puncture extending from a patient's skin to a blood vessel or other body lumen.

In accordance with one embodiment, an apparatus is provided for providing hemostasis within a puncture extending through tissue. The apparatus includes an elongate tubular member having proximal and distal ends defining a longitudinal axis therebetween, and a lumen extending between the proximal and distal ends. The elongate member may include an expandable member, e.g., a balloon, disposed on or adjacent to the distal end, and a hub on the proximal end that includes an interior communicating with the lumen of the elongate member. The hub may include a valve communicating with the interior, and a plunger having a fluid port thereon that is movable into and out of the valve.

For example, in one embodiment, the valve may be a one-way valve allowing fluid to be delivered into the interior of the hub. When fluid is delivered into the interior, the fluid may travel through the lumen to expand the expandable member. The plunger may be advanceable into the valve to open the valve and allow fluid to be evacuated from the interior. Optionally, the valve may automatically close when the plunger is withdrawn to substantially seal any remaining fluid within the interior. In addition or alternatively, the plunger may be biased such that when the plunger is released, it automatically withdraws from the valve, allowing the valve to close again to its one-way configuration.

The apparatus may also include a piston movable within the interior, and a pressure indicator coupled to the piston. The pressure indicator may be used to determine when the expandable member is expanded to a predetermined size and/or shape, e.g., when a predetermined volume of fluid is directed into the interior. For example, when fluid is delivered into the interior through the valve, the piston may move proximally until the pressure indicator is visible, indicating a desired volume of fluid has been delivered into the interior to expand the expandable member. In one embodiment, the piston may be coupled to a distal end of the expandable member such that the piston moves proximally as fluid is directed into the interior, thereby shortening the expandable member as it expands.

Optionally, the hub may include a pressure relief feature to avoid over-pressurization, e.g., to prevent the expandable member from expanding beyond a desired size and/or shape. In one embodiment, the pressure relief feature may be an evacuation port adjacent the piston that communicates with the interior of the hub when the piston moves to a predetermined proximal position, corresponding to a predetermined pressure and/or volume of the fluid within the interior. The evacuation port may communicate with a reservoir or vent to atmosphere, thereby allowing excess fluid to be evacuated from the interior when the predetermined pressure is exceeded. Alternatively, the pressure relief feature may be a valve that opens when a predetermined pressure within the interior is exceeded, allowing fluid within the interior to leak or otherwise escape from the hub.

In another embodiment, an apparatus for providing hemostasis within a puncture through tissue includes an elongate tubular member having proximal and distal ends defining a longitudinal axis therebetween, and a lumen extending between the proximal and distal ends. The elongate member has an expandable member disposed at or adjacent to the distal end that is expandable between collapsed and enlarged conditions, and a hub on the proximal end. The hub may include an interior communicating with the lumen of the elongate member, and a piston slidable within the interior.

The piston may be coupled to the expandable member and may be biased to a distal position within the hub to extend the expandable member in the collapsed condition. The hub may include a valve for receiving a source of fluid therethrough, e.g., a fluid port coupled to a plunger, to deliver or aspirate fluid from the interior. When fluid is delivered into the interior and the lumen to expand the expandable member, the piston may be directed proximally against the bias, thereby shortening the expandable position as it expands. A pressure indicator may be coupled to the piston that provides a visual or other indicator when sufficient fluid is delivered to expand the expandable member to a desired size and/or shape. When fluid is evacuated from the interior via the valve, the piston may resiliently return towards the distal position, thereby extending the expandable member as it collapses.

Optionally, the hub may include a pressure-relief feature and/or a one-way valve-plunger mechanism. In addition or alternatively, the apparatus may include an introducer or other sheath, including proximal and distal ends, and a sheath lumen extending therebetween sized for receiving the elongate member therein when the expandable member is collapsed. In addition, a source of sealing compound may be provided that may be coupled to the proximal end of the sheath for delivering a sealing compound into the sheath lumen through the tubular member. In exemplary embodiments, the source of sealing compound may include multiple polymers that may be mixed and/or otherwise injected as a liquid, or a solid plug or carrier.

In accordance with another embodiment, a method is provided for providing hemostasis of a puncture, e.g., extending through tissue and/or communicating with a body lumen. In an exemplary embodiment, the body lumen may be a blood vessel, e.g., a femoral, carotid, or other peripheral artery. Initially, an apparatus may be provided that includes an elongate tubular member having a distal end carrying an expandable member, and a proximal end including a hub.

The distal end of the tubular member may be introduced into the puncture until the expandable member is disposed within the body lumen. Fluid may be introduced into the hub through a one-way valve. As fluid enters the hub, the fluid may pass through the tubular member to expand the expandable member within the body lumen. In one embodiment, fluid delivery may continue until a pressure indicator on the hub indicates that the expandable member has been expanded to a desired size and/or shape. Optionally, fluid delivery may cause the expandable member to shorten as it expands.

With the expandable member expanded, the apparatus may be at least partially withdrawn from the puncture until the expandable member contacts a wall of the body lumen, thereby substantially sealing the puncture from the body lumen. Optionally, a sealing material, e.g., a multiple component liquid sealing compound and/or a solid plug or carrier, may be introduced into the puncture around the tubular member to enhance hemostasis.

Fluid may be evacuated from the expandable member by overcoming the one-way nature of the valve, e.g., by directing a nipple, plunger, or other element into the valve. For example, a plunger may be advanced through the valve such that fluid in the hub escapes through the valve or is aspirated into a syringe or other source of vacuum. As fluid is evacuated from the hub, the expandable member may collapse and/or extend. With the expandable member collapsed, the apparatus may be withdrawn completely from the puncture, e.g., through the sealing material if such material is delivered into the puncture.

Optionally, pressure may be applied to skin overlying the body lumen, e.g., to at least partially suppress fluid flow through the body lumen as the apparatus is withdrawn from the puncture.

In one embodiment, before using the apparatus, an introducer or other sheath may be introduced through the puncture into the body lumen, and the apparatus may be introduced into the puncture through the introducer. With the apparatus sealing the puncture from the body lumen, sealing material may be introduced into the puncture, e.g., through and/or around the introducer. While or after delivering the sealing material into the puncture, the introducer may be withdrawn from the puncture, e.g., before or after removing the apparatus.

Other aspects and features of the present invention will become apparent from consideration of the following description taken in conjunction with the accompanying drawings.

DETAILED DESCRIPTION

Turning to the drawings, FIGS. 1-7 show an exemplary embodiment of an apparatus 2 for providing temporary hemostasis within a puncture extending through tissue (not shown, see, e.g., FIGS. 8A-8F). Generally, the apparatus 2 includes an elongate member 4 having a balloon or other expandable member 6, a hub subassembly 8, and a source of inflation media, e.g., syringe 10, coupled to the hub subassembly 8, e.g., via a conduit 12, such as flexible tubing and the like.

Figure 1:
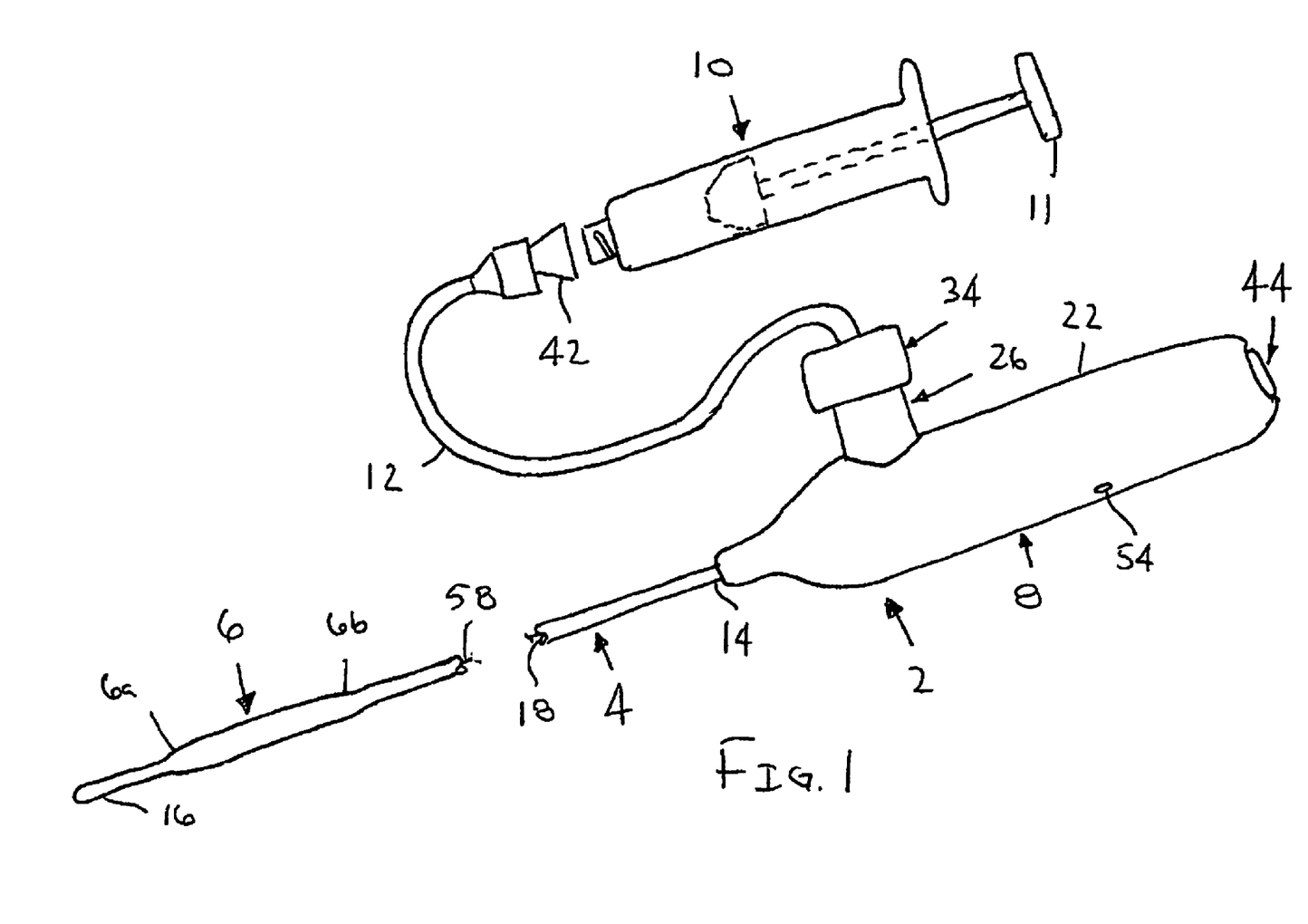
FIG. 1 is a side view of an exemplary embodiment of an apparatus for temporary hemostasis, including a balloon on a distal end and a hub on a proximal end of the apparatus with a one-way valve for delivering fluid into the hub to expand the balloon.
Figure 2:
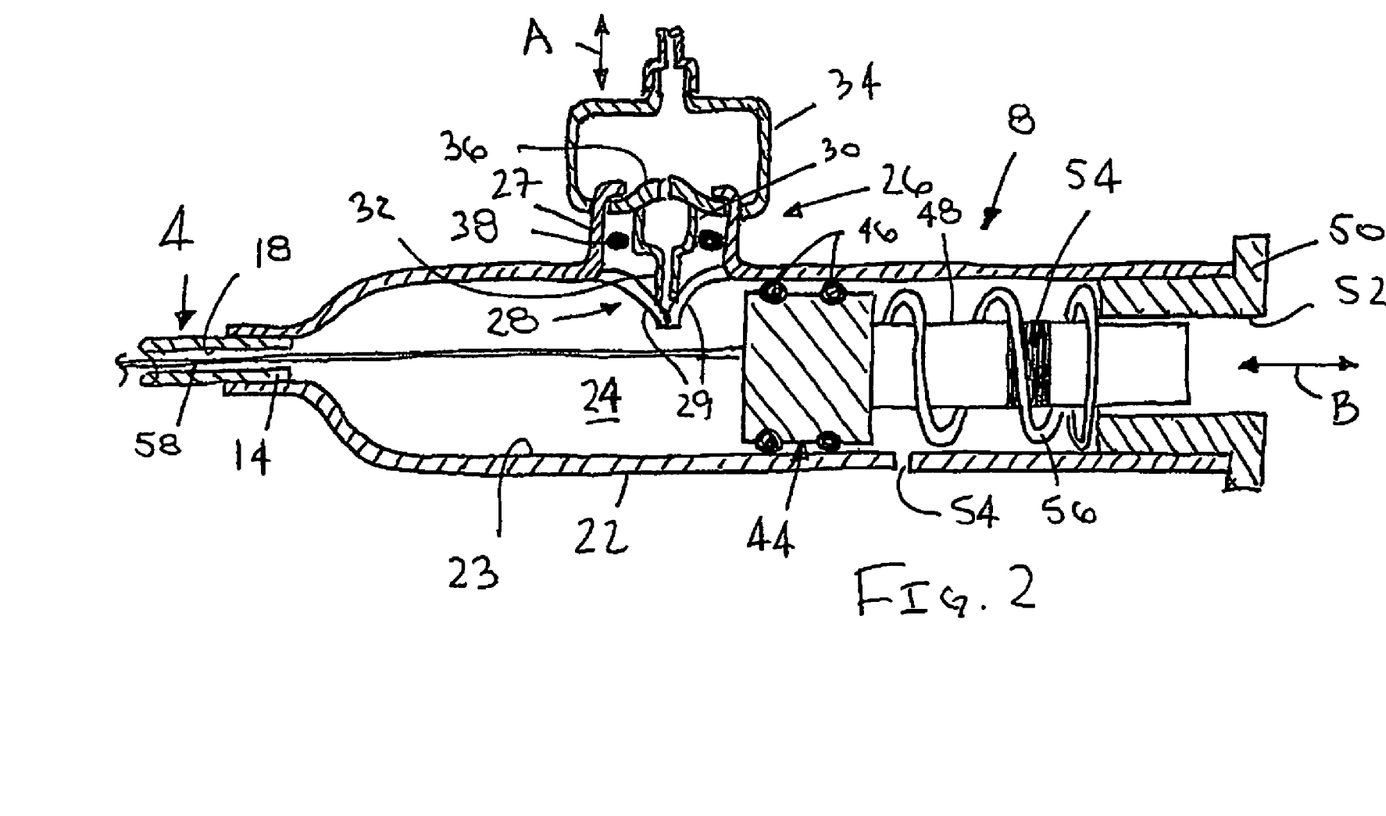
FIG. 2 is a cross-sectional side view of the hub of the apparatus of FIG. 1, showing a button shown in an "up" position, which may be used to open the one-way valve.

With particular reference to FIGS. 1 and 2, the elongate member 4 may be an elongate tubular body including a proximal end 14, a distal end 16, and a lumen 18 extending therebetween, thereby defining a longitudinal axis 20. The elongate member 4 may be flexible, semi-rigid, or rigid, e.g., having a uniform or variable flexibility along its length. The elongate member 4 may be formed from a variety of materials providing a desired rigidity, e.g., plastic, such as polyamide, PEEK, nylon, PET, PEBAX, polyethylene, and/or metal, such as stainless steel or a nickel-titanium alloy, and may be fabricated using known processes, e.g., extrusion, roll forming, machining, and the like. Optionally, a lubricious coating (not shown) may be provided on an exterior of the elongate member 12, e.g., DOW 360 silicone fluid.

In one embodiment, the distal end 16 may be substantially flexible such that the distal end 16 may curve, bend, or otherwise conform substantially to the contour of a puncture and/or body lumen (not shown) into which the distal end 16 is advanced. The distal end 16 of the elongate member 4 may have a size sufficient to be inserted into a relatively small puncture and/or body lumen. For example, the distal end 16 (and possibly the remainder of the elongate member 4) may have an outer diameter between about 0.010-0.030 inch (0.25-0.75 mm), or less than about 0.020 inch (0.5 mm).

Still referring to FIGS. 1 and 2, the hub subassembly 8 generally includes a housing 22 affixed to the proximal end 14 of the elongate member 4. The housing 22 includes an interior or cavity 24 that communicates with the lumen 18 of the elongate member 4, and a valve assembly 26 for accessing the interior 24. In one embodiment, the valve assembly 26 may include a one-way valve, such as a duckbill valve 28. The duckbill valve 28 may include mating flaps 29 that may be selectively opened to allow communication with the interior 24. For example, the valve 28 may be configured such that the flaps 29 open automatically when the pressure is greater within the valve assembly 26 than within the interior 24, but otherwise are biased to close together to provide a substantially fluid-tight seal.

The valve assembly 26 may also include a plunger or nipple 30 having an outer cap 36 and a fluid port 32 extending from the cap 36. The nipple 30 may be movable within valve housing 27 in a direction represented by arrow A shown in FIG. 2, e.g., to direct the nipple 30 between the flaps 29 to open or otherwise overcome the bias of the valve 28, as explained further below. Optionally, a cover or button 34 may be provided over the valve assembly 26 that may be coupled to the cap 36, e.g., to facilitate directing the nipple 30 downwardly or otherwise into the valve 28.

Figure 3:
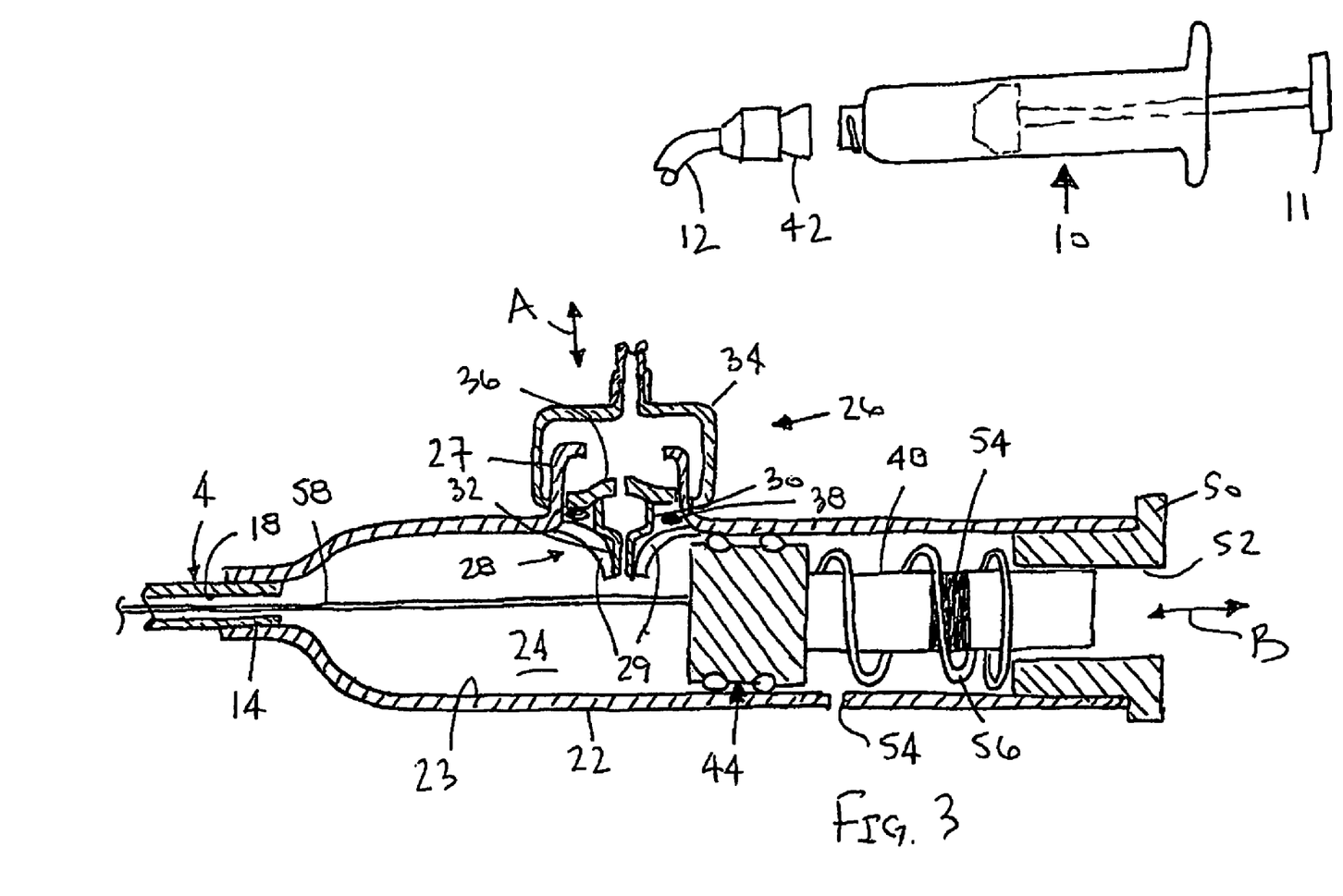
FIG. 3 is a cross-sectional side view of the hub of FIG. 2 with the button in a "down" position, allowing fluid to be evacuated from within the hub.

Still referring to FIG. 2, the nipple 30 may be moved by depressing the button 34 or cap 36. The button 34 may be able to toggle between "up" and "down" positions, as shown in FIGS. 2 and 3, respectively. In one embodiment, the button 34 may be biased towards the "up" position, e.g., by a spring or other biasing device (not shown) disposed within the valve assembly 26, for example, between the button 36 and the flaps 29. Alternatively, the button 34 may be releasably securable in the down position using any number of known mechanisms, e.g., one or more detents, latches, and the like, such that the button 34 may be alternately securable in the "up" and "down" positions. The nipple 30 may be sealed in the valve assembly 26, e.g., using an o-ring 38 or similar seal, that provides a substantially fluid-tight seal, yet allows the nipple 30 to move between the "up" and "down" positions.

The nipple 30 may communicate through the valve housing 27 and/or button 34 with a conduit, such as flexible tubing 12 and the like, that may terminate in a connector 42, such as a male or female Luer lock connector 42. The connector 42 may be configured to connect or otherwise mate with a syringe 10 or other source of inflation media, e.g., to allow fluid infusion/evacuation, as described further elsewhere herein.

Still referring to FIG. 2, the hub subassembly 8 includes a piston 44 slidable within the housing 22, e.g., axially in a direction represented by arrow B in FIG. 2. The piston 44 may include a seal 46, for example, one or more o-rings and the like, that may form a substantially fluid-tight seal between the piston 44 and an inner surface 23 of the housing 22, yet allow the piston 44 to move axially within the housing 22. Consequently, fluid may be prevented from passing proximally past the seal 46 between the piston 44 and the housing 22.

Optionally, the hub subassembly 8 may include a pressure relief feature 54 that may cooperate with the piston 44 to prevent over-pressurization, as explained further below. For example, as shown, the pressure relief feature 54 may be a side port or other opening in the housing 22 adjacent the piston 44. When the piston 44 is in a distal position, such as that shown in FIGS. 2 and 3, the pressure relief feature 54 may be substantially isolated from the interior 24. When the piston 44 moves proximally to a proximal position, such as that shown in FIG. 4, the pressure relief feature 54 may communicate with the interior 24, as explained further below. In an alterative embodiment, the pressure relief feature may be a relief valve (not shown) in the hub subassembly 8 adjacent the interior 24 that may open when a predetermined pressure is exceeded.

A pressure indicator may be provided on or otherwise coupled to the piston 44. In one embodiment, the piston 44 may include a shaft or member 48 that projects proximally from the piston 44 and carries a visual or other indicator 54. For example, as shown in FIGS. 2-4 and 6, the pressure indicator 54 may be a colored band around the shaft 48 or other proximal portion of the piston 44. Optionally, other pressure indicators may be provided that indicate when the piston 44 has moved to a predetermined proximal position within the housing 22, e.g., cooperating detents that "click" or provide other audible and/or tactile feedback to the user.

Figure 4:
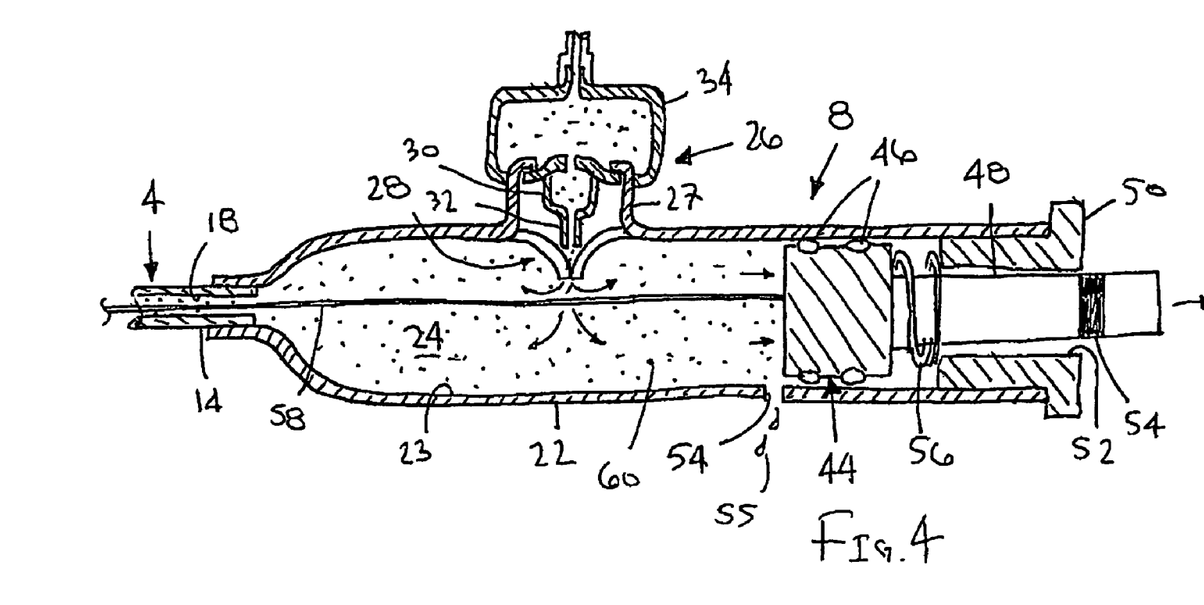
FIG. 4 is a cross-sectional side view of the hub of FIG. 2, illustrating fluid being delivered from a syringe into the hub with the button in the "up" position. As fluid is introduced into the hub, a pressure indicator may project proximally from the hub.

With reference still to FIG. 2, the hub subassembly 8 may also include an abutment or proximal end 50 having an orifice 52 sized to permit the shaft 48 of the piston 44 to pass therethrough, e.g., to expose the pressure indicator 48, as shown in FIG. 4. In this regard, the pressure indicator 48 may be able to move proximally and project outwardly from the proximal end 50 of the hub subassembly 8. In the embodiment shown, the pressure indicator 48 includes a visual indicator 54, e.g., a color band surrounding all or a part of the pressure indicator 48. The visual indicator 54 may provide a visual indication that a predetermined pressure and/or volume of fluid has been introduced into the hub subassembly 8, e.g., to expand the balloon 6 to a desired size and/or shape.

For example, the predetermined pressure may correspond to a desired pressure for the balloon 6, e.g., to ensure that the balloon 6 is expanded to a desired diameter and/or to prevent risk of the balloon 6 rupturing. Alternatively, the visual indicator 54 may include a series of graduations or other indicia (not shown) that may be used to ascertain the degree of expansion of the balloon 6.

Optionally, the piston 44 may be biased, e.g., towards the proximal or distal position. For example, as seen in FIG. 2, an extension spring 56 or other biasing member may be coupled between the piston 44 and at the other end to the abutment 50. The spring 56 may bias the piston 44 towards the distal position, i.e., tending to move the piston 44 distally absent any pressure from fluid in the interior 24 of the housing 22.

In one embodiment, the piston 44 may be coupled to the expandable member 4 to shorten or extend the balloon 6 as the piston moves relative to the hub subassembly 8. For example, a wire, filament, or other connector member 58 may be secured at one end to the piston 44 and at its other end to a distal end 6a of the balloon 6 or distally beyond the balloon 6. When fluid is introduced into the interior 24 of the hub subassembly 8, the piston 44 may move proximally, e.g., toward the hub subassembly abutment 50 against the bias of the spring 56. Movement of the piston 44 proximally thereby applies tension or otherwise pulls the connector member 58 proximally, which shortens the balloon 6, e.g., to facilitate creating a toroidal shape when the balloon 6 is expanded.

Figure 5:
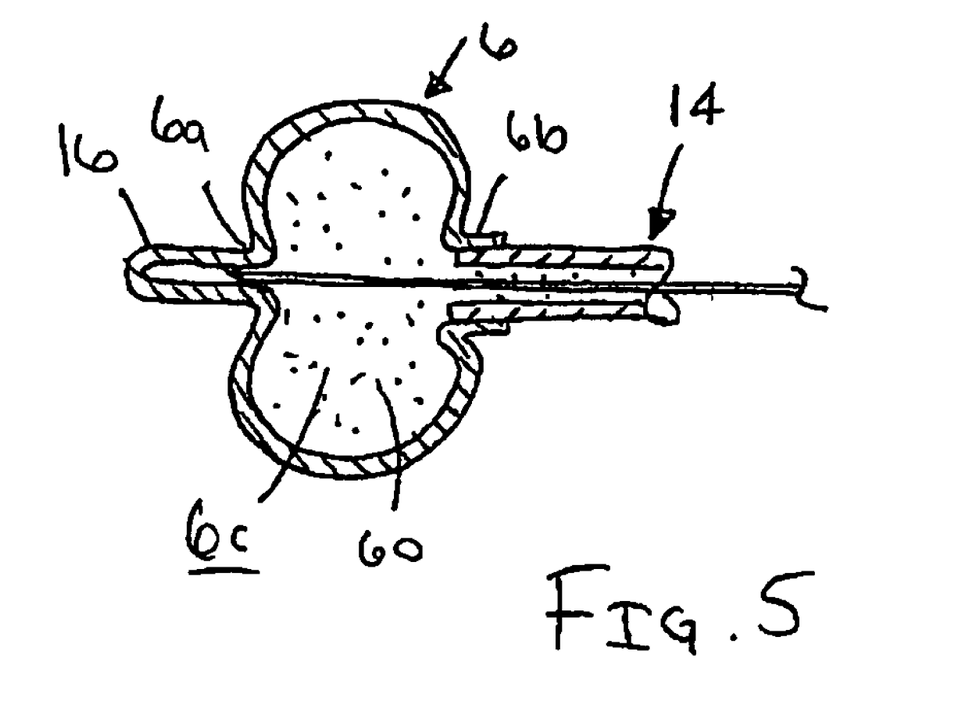
FIG. 5 is a cross-sectional side view of the balloon of FIG. 1 being expanded as fluid is delivered into the hub. The balloon may be expanded to a desired size when the pressure indicator projects from the hub, as shown in FIG. 4.
Figure 7:
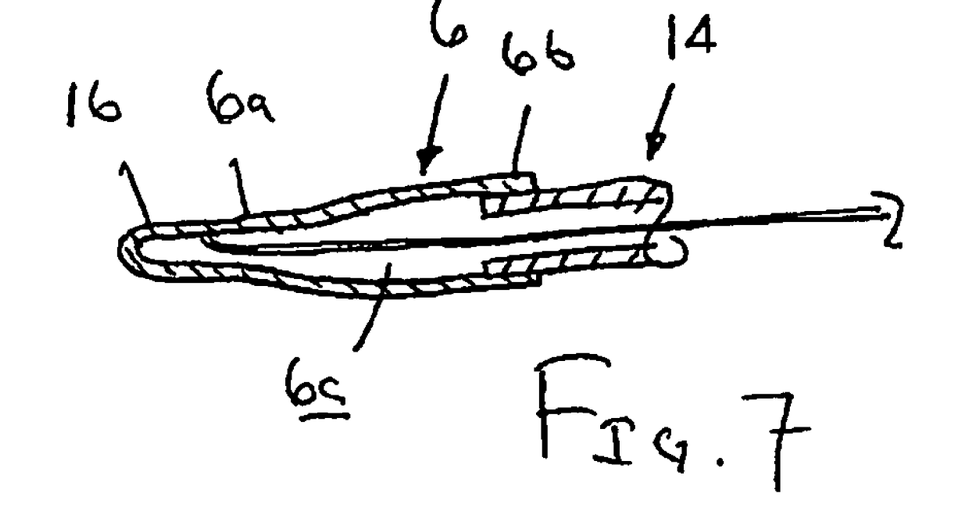
FIG. 7 is a cross-sectional side view of the balloon of FIG. 1 being collapsed as fluid is evacuated from the hub.

With reference to FIGS. 1, 5, and 7, the balloon 6 may be an expandable body expandable between a contracted condition (such as that shown in FIGS. 1 and 7) and an enlarged condition (such as that shown in FIG. 5). The balloon 6 may be formed from a flexible, substantially inelastic material, e.g., a nonelastomeric material, such as PET, nylon, polyethylene, polyurethane, PEBAX, and the like. For example, the balloon 6 may be a substantially noncompliant body that may expand to a predetermined size once a minimum pressure is introduced into its interior. In this embodiment, the size of the balloon 6 in the enlarged condition may be substantially fixed. Alternatively, the balloon 6 may be formed from an elastic material, such that the size in the enlarged condition is dependent upon the pressure or volume of fluid delivered within the balloon 6, as is known in the art.

As best seen in FIGS. 1 and 5, the distal end 6a of the balloon 6 may be extended distally to provide a floppy or otherwise substantially atraumatic tip for the apparatus 2. In an exemplary embodiment, the distal end 6a of the balloon 6 may have a length of at least about fifty millimeters (50 mm).

In the contracted condition, the balloon 6 may conform substantially to the diameter of the elongate member 4. In one embodiment, tension may be applied between the proximal and distal ends of the balloon 6 by the connector member 58 such that the balloon 6 is under slight axial tension in the contracted condition, which may minimize risk of the balloon 6 expanding, kinking, otherwise increasing in cross-section and/or catching on anything contacted by the balloon 6.

Turning to FIGS. 4 and 7, the balloon 6 may be expanded to the enlarged condition by introducing inflation media 60 into the interior 24 of the housing 22, through the lumen 18 of the elongate member 4, and, consequently, into the interior 6c of the balloon 6. The inflation media 60 may be a substantially incompressible fluid, e.g., saline, or a compressible fluid, such as carbon dioxide, nitrogen, or air. As fluid 60 is introduced into the interior 24 of the housing 22, the fluid pressure within the interior 24 may exceed the bias of the spring 56, causing the piston 44 to move proximally within the housing 22, thereby pulling the wire 58 and shortening the balloon 6 as it expands.

Additional information on possible construction of the expandable member 6 or other components of the apparatus 2 may be found, for example, in co-pending application Ser. No. 10/454,362, filed Jun. 4, 2003, and Ser. No. 10/806,952, filed Mar. 22, 2004. The entire disclosures of these references are expressly incorporated by reference herein.

Optionally, as shown in FIGS. 8A-8F, the apparatus 2 may include other components, e.g., to provide a kit for performing a procedure on a patient. For example, an introducer or other access or delivery sheath 62 may be provided that includes a proximal end 64, a distal end 65, and a lumen 66 extending therebetween. The introducer sheath 62 may include a tapered distal tip 67, e.g., for facilitating advancing the introducer sheath 62 through a puncture, as is known in the art.

Figure 8A:
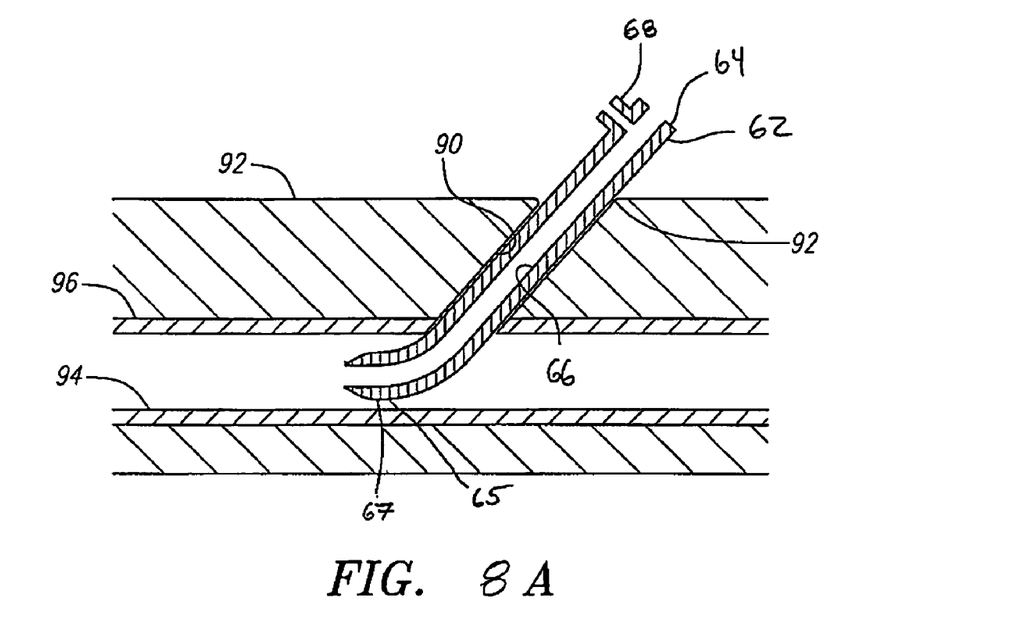
FIGS. 8A-8F are cross-sectional views of a puncture extending through tissue to a body lumen, showing a method for sealing the puncture.
Figure 8B:
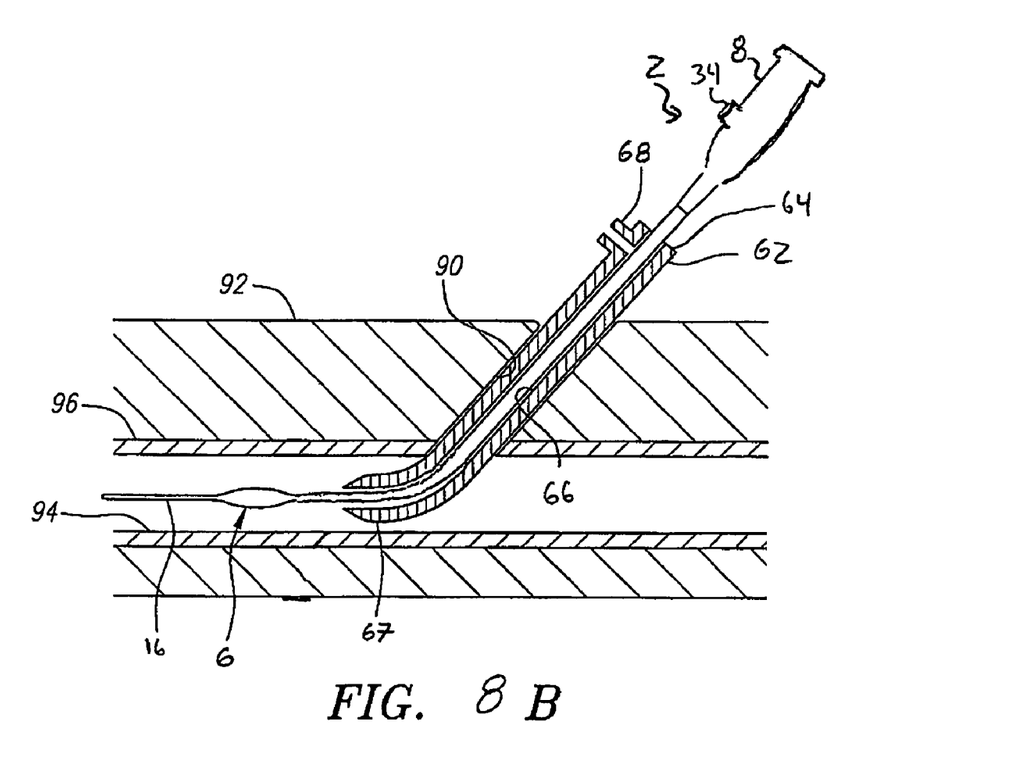

In addition, the introducer sheath 62 may include a side port 68 on the proximal end 64 communicating with the lumen 66 and/or may include one or more seals (not shown), e.g., to prevent substantial proximal flow of fluid through the lumen 66, also as is known in the art. As shown in FIG. 8E, a source of sealing compound 130 may be connectable to the side port 68, e.g., for delivering a sealing compound 146 into the lumen 66 of the introducer sheath 62.

With continued reference to FIG. 8E, a dual syringe assembly 130 may be provided that includes two components of a sealing compound. In an exemplary embodiment, a polymer precursor may be provided in each syringe 132 of the syringe assembly 130. A "Y" fitting 140 may be provided that includes proximal sections 142 that communicate with a single distal section 144. The proximal and distal sections 142, 144 may include connectors, e.g., luer lock connectors and the like (not shown), for connecting with outlets 136 of the syringes 132 and with the side port 68 of the introducer sheath 62. Thus, the "Y" fitting 140 may be connectable to outlets 136 of the syringes 132 such that the components ejected out of the syringes 132 may mix before being delivered into the side port 68 of the introducer sheath 62. The "Y" fitting 140 may include one or more components, e.g., separate lengths of tubing and the like (not shown), as will be appreciated by those skilled in the art. In one embodiment, the components are polymer precursors that mix to create a hydrogel. Additional information on hydrogels and systems and methods for delivering them may be found in U.S. Pat. Nos. 6,152,943, 6,165,201, 6,179,862, 6,514,534, and 6,379,373, and in co-pending applications publication Nos. 2002-0106409 published on Aug. 8, 2002, 2003-0012734 published on Jan. 16, 2003, 2002-0114775 published on Aug. 22, 2002, and 2004-0249342 published on Dec. 9, 2004. The disclosures of these references and any others cited therein are expressly incorporated by reference herein.

Figure 8C:
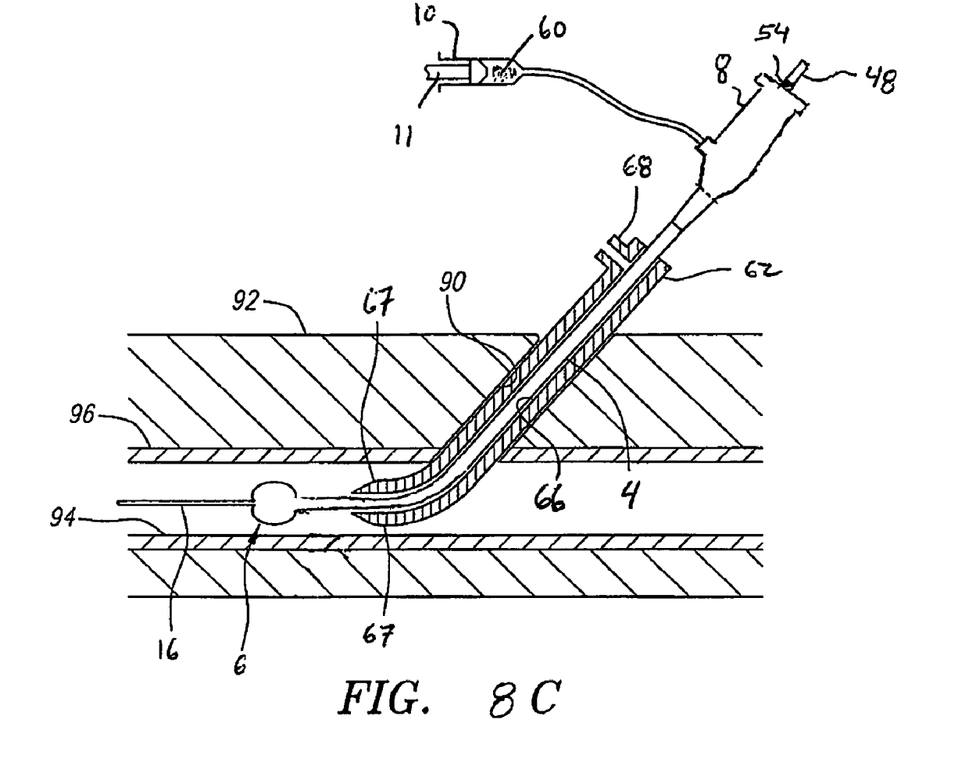
Figure 8D:
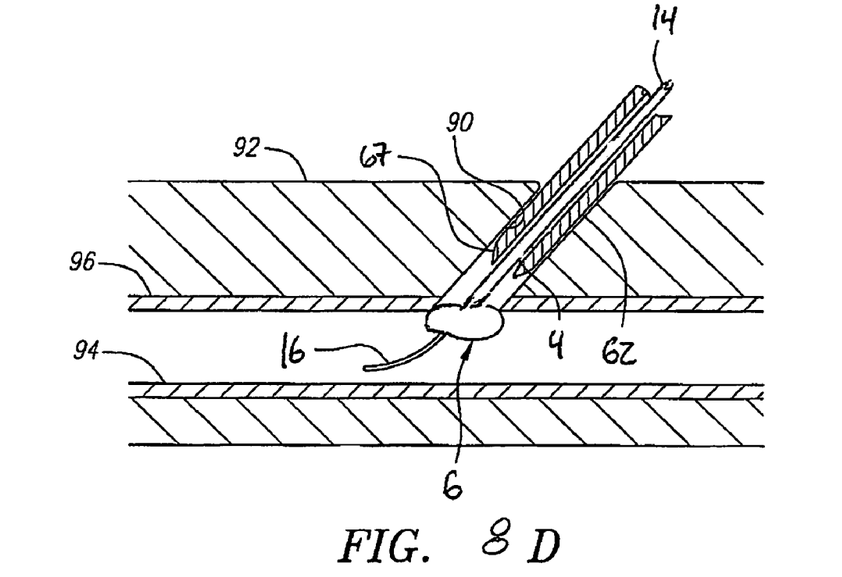
Figure 8E:
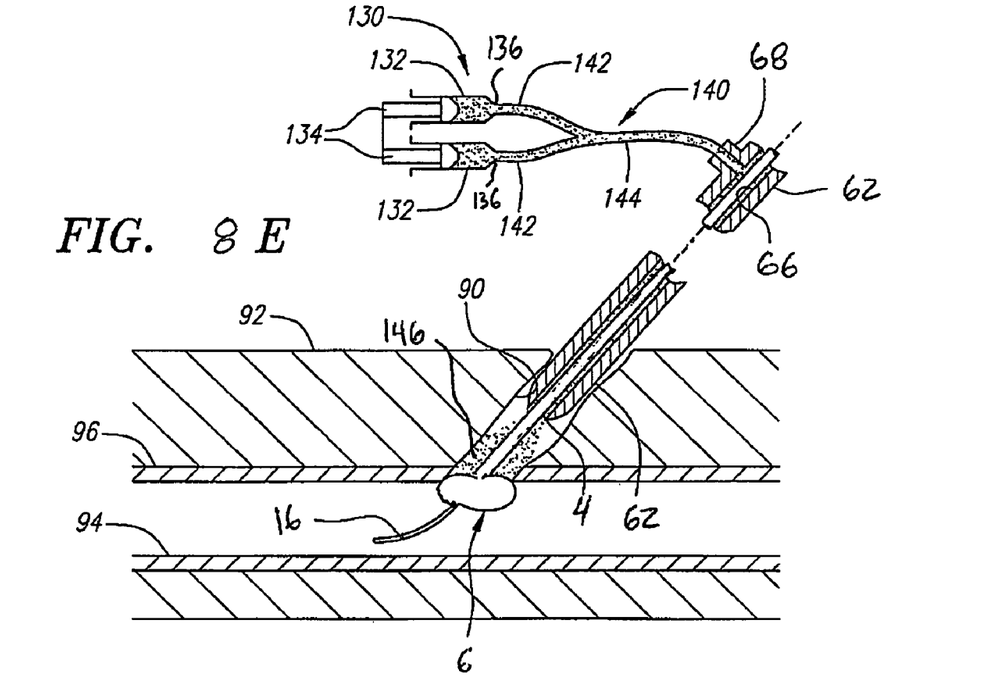
Figure 8F:
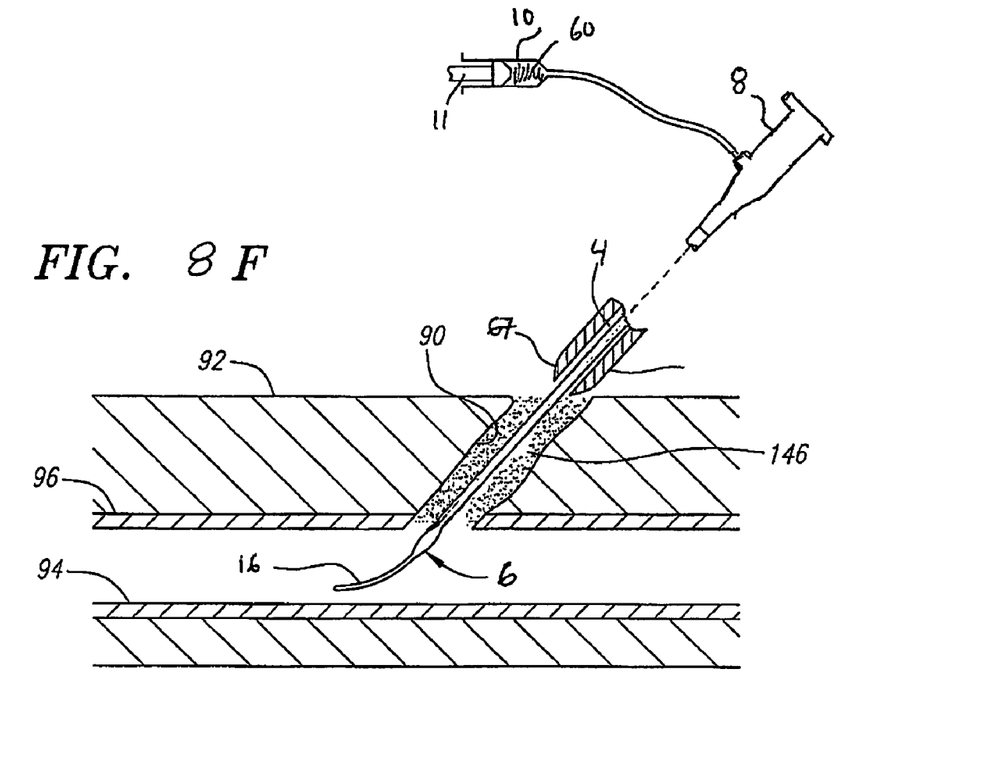

In addition, the kit may include a syringe 10 (as shown in FIGS. 8C and 8F) or other source of inflation media 60 that may be coupled to the hub subassembly 8, as explained above. Optionally, the kit may also include a stylet or obturator (not shown) that may be inserted into the lumen 66 of the introducer sheath 62, e.g., to facilitate percutaneously inserting the introducer sheath 62 through tissue. In addition or alternatively, one or more guidewires (not shown) may also be provided.

Turning to FIGS. 8A-8F, an exemplary method for sealing a passage through tissue is shown. In an exemplary embodiment, the passage is a percutaneous puncture 90 extending from a patient's skin 92 through tissue to a blood vessel or other body lumen 94. For example, the vessel 94 may be a peripheral artery, e.g., a femoral artery, a carotid artery, radial artery, and the like.

Initially, as shown in FIG. 8A, an introducer sheath 62 may be placed within the puncture 90 such that the distal tip 67 is disposed within the vessel 94. For example, a stylet having a sharpened distal tip (not shown) may be inserted through the lumen 66 of the introducer sheath 62 such that the sharpened distal tip extends beyond the distal tip 67 of the introducer sheath 62. The introducer sheath 62 and stylet may then be inserted directly through the patient's skin 92 until the distal tip 67 is disposed within the vessel 94. Alternatively, the introducer sheath 62 may be advanced over a guidewire previously inserted through the puncture 90 into the vessel 94, using known procedures.

One or more instruments (not shown) may be advanced through the introducer sheath 62 and into the vessel 94, e.g., to perform one or more diagnostic and/or therapeutic procedures within the patient's body. The one or more instruments may include catheters, e.g., balloon catheters, stent delivery catheters, imaging catheters, and the like, guidewires, and/or other devices. Upon completing the procedure(s), any instruments may be removed and the puncture 90 may be sealed using an apparatus, such as that shown in FIGS. 1-7 and described above.

For example, turning to FIG. 8B, with the balloon 6 in the contracted condition, the distal end 16 of the apparatus 2 may be inserted through the lumen 66 of the introducer sheath 62 until the balloon 6 is disposed within the vessel 94. Optionally, the apparatus 2 may include one or more markers, e.g., radiopaque markers (not shown), to facilitate monitoring insertion of the apparatus 2 using external imaging, e.g., fluoroscopy, ultrasound, magnetic resonance imaging ("MRI"), and the like.

Alternatively or in addition, one or more visual markers (not shown) may be provided, e.g., on the proximal end 14 of the elongate member 4. The markers may include one or more colored bands at predetermined locations along a length of the elongate member 4 relative to the balloon 6. For example, a distance between a band on the proximal end 14 of the elongate member 4 may correspond to a length of the introducer sheath 62, thereby providing a visual indication when the apparatus 2 has been advanced sufficiently to expose the balloon 6 beyond the distal tip 67 of the introducer sheath 62.

Optionally, with additional reference to FIGS. 1-6, the balloon 6 and/or apparatus 2 may be prepared before insertion into the introducer sheath 62 and/or puncture 90, e.g., to collapse the balloon 6. For example, syringe 10 (or other source of vacuum) may be secured to the connector 42 on the end of the conduit 12. The button 34 may be depressed, thereby pushing down the nipple 30 such that the fluid port 32 is exposed to the interior 24 of the housing 22, as shown in FIG. 3. With the nipple 30 advanced through the valve 28, the valve 28 may be opened, allowing fluid within the interior 24 of the housing 22 to be evacuated. For example, plunger 11 on the syringe 10 may be pulled proximally to draw a vacuum in the syringe 10, thereby evacuating any air or other fluid within the interior 24 of the housing 22. Consequently, any residual air or other fluid within the balloon 6 may also by evacuated, enhancing collapsing the balloon 6.

The button 34 may then be released or otherwise returned to the "up" position, shown in FIG. 2, retracting the nipple 30 and fluid port 32 out of the valve 28, thereby substantially sealing the fluid path to the balloon 6 from ambient pressure outside apparatus 2. This preparation, i.e., subjecting the balloon 6 to a vacuum before insertion, may minimize the profile of the balloon 6 in the contracted condition, which may facilitate inserting the apparatus 2 into the introducer sheath 62 and/or puncture 90.

Turning to FIG. 8C, once the collapsed balloon 6 is advanced through the introducer sheath 62 into the vessel 94, the balloon 6 may be expanded to the enlarged condition. For example, a source of inflation media may be connected to connector 42 of the hub subassembly 8. Alternatively, other sources of inflation media may be attached to the connector 42 on the conduit 12. The syringe 10 may be the same or different from the syringe 10 used to evacuate the fluid path to the balloon 6.

As shown in FIG. 4, plunger 11 of syringe 10 may be advanced distally, forcing inflation media 60 into the internal 24 of the housing 22. This causes the inflation media 60 to pass through the valve assembly 26, opening the flaps 29 of the valve 28, allowing the inflation media 60 to enter the interior 24 of the housing 22. The inflation media 60 may travel along the fluid path to the balloon 6, i.e., into the interior 24, through the lumen 18, and into the interior 6c of the balloon 6, as shown in FIG. 5.

As the plunger 11 of the syringe 10 is depressed, fluid pressure builds within the interior 24 of the housing 22 and lumen 18, causing the balloon 6 to inflate to the enlarged condition. Simultaneously, the increasing fluid pressure may also cause the piston 44 (and pressure indicator 48) to move proximally, as shown in FIG. 4. In one embodiment, the plunger 11 is depressed until the visual indicator 54 projects from the abutment 50 of the hub subassembly 8. When the visual indicator 54 is in this position, the user may be informed that a desired pressure or volume has been achieved within the balloon 6, which may correspond to a desired size and/or shape for the balloon 6, such as that shown in FIG. 5.

If additional fluid is delivered into the hub subassembly 8 after the desired volume and/or pressure is achieved, the hub subassembly 8 may include a pressure relief feature to prevent over-inflation of the balloon 6, which may otherwise damage or even break the balloon 6. For example, the pressure relief feature may be a side port 54 located in the housing 22 at a location adjacent the piston 44. When the piston 44 is directed proximally such that the visual indicator 54 appears, the side port 54 may remain substantially isolated from the interior 24 of the housing 22.

If additional fluid is delivered, the piston 44 may move proximally beyond this position, thereby exposing the interior 24 of the housing 22 to the side port 54. This exposure causes any excess fluid (represented by drops 55) from escaping through the side port 54 until the piston 44 returns to the proximal position where the side port 54 is no longer exposed to the interior 24. Thus, the side port 54 may provide a safety feature, allowing only a predetermined pressure and/or volume being present within the interior 24 of the housing 22. As shown in FIG. 5, in the enlarged condition, the balloon 6 may be expanded to a desired diameter and shortened to provide a toroidal shape.

Turning to FIG. 8D (which omits the proximal components of the apparatus 2 merely for simplicity), the apparatus 2 may be partially withdrawn from the puncture 90 with the balloon 6 in the enlarged condition, i.e., until the balloon 6 engages the puncture 90. The balloon 6 may substantially seal the puncture 90, i.e., substantially isolating the puncture 90 from the interior of the vessel 94. Thus, the apparatus 2 may provide temporary hemostasis, e.g., preventing blood from passing through the puncture 90. Thus, even without the additional steps that follow, the apparatus 2 may be used to provide hemostasis in emergency situations in order to minimize loss of blood until a puncture victim may be treated.

As explained above, the balloon 6 may at least partially evert in the enlarged condition, which may provide hemostasis, while still allowing blood flow to continue along the vessel 94. For example, as shown in FIG. 8D, the diameter of the balloon 6 may be substantially greater than its length in the enlarged condition. Thus, when the balloon 6 is pulled into engagement with the wall 96 of the vessel 94, at least a portion of the vessel 94 lumen may remain unobstructed, as shown.

Optionally, in order to maintain the balloon 6 substantially against the puncture 90 without requiring an individual to hold the apparatus 2, a tensioner or other external device (not shown) may be provided that may apply a proximal force to the apparatus 2 to maintain the balloon 6 substantially against the puncture 90, as disclosed in application Ser. Nos. 10/454,362 and 10/806,952, incorporated by reference above.

Optionally, turning to FIG. 8E, a sealing compound 146 may be delivered into the puncture 90. For example, the sealing compound 146 may be a liquid or other flowable material that may be introduced into the puncture 90. Because of the hemostasis provided by the balloon 6, the sealing compound 146 may be delivered without substantial concern that the sealing compound 146 may leak into the vessel 94.

In an exemplary embodiment, the sealing compound may include multiple component polymer precursors that create a hydrogel when mixed together. Such a sealing compound may be particularly useful, because it may be substantially harmless to the patient even if it somehow leaks into the vessel 94. In fact, such polymer precursors, if leaked into a vessel, may simply dilute and flow away, where they may be metabolized naturally without substantial risk of creating thrombus. This is another reason why it may be useful to seal the puncture 90 with an everted balloon 6, while still allowing fluid to continue to flow along the vessel 94, as described above. If the hydrogel leaks into the vessel 94 around the balloon 6, blood flow may dilute and carry the hydrogel away, where it may be safely metabolized naturally, e.g., by the liver.

As shown in FIG. 8E, a two-part sealing compound 146 is shown contained within a dual syringe assembly 130. The polymer precursors or other components in the syringes 132 may be mixed or otherwise prepared using known procedures. The plungers 134 of the syringes 132 may be linked such that they may be depressed substantially simultaneously, thereby delivering the precursors simultaneously. The precursors may mix in the "Y" fitting 140 into a liquid sealing compound 146, and then be delivered into the side port 68 of the introducer sheath 62. Alternatively, an auto injector device, including a spring, motor, pneumatic pressure, and the like (not shown) may be provided for delivering the precursors at a desired substantially continuous rate, as disclosed in application Ser. No. 10/806,952, incorporated by reference above. Such a device may prevent unintended pauses during delivery, which may cause the "Y" fitting 140 or other passages through which the sealing compound passes from becoming obstructed.

The liquid sealing compound 146 may be delivered through the lumen 66 of the introducer sheath 62 out the distal tip 67 into the puncture 90. The introducer sheath 62 may remain stationary as the sealing compound 146 is delivered, thereby allowing the sealing compound to flow into the puncture 90 around the introducer sheath 62. Alternatively, the introducer sheath 62 may be withdrawn proximally from the puncture 90 as the sealing compound 146 is delivered, thereby filling the puncture tract with the sealing compound 146, as shown in FIG. 8F. Optionally, other components (not shown) may be provided on the apparatus 2 and/or introducer sheath 62 to enhance delivery of the sealing compound, as disclosed in application Ser. No. 10/454,362, incorporated by reference above.

It will be appreciated that other devices may be used for delivering sealing material or even a sealing device into the puncture 90. For example, other apparatus for delivering liquid sealing compounds, including single or multiple lumens (not shown), may be advanced over the apparatus 2, e.g., through the introducer sheath 62. Alternatively, the introducer sheath 62 may be removed, before such delivery apparatus are advanced over the apparatus 2 into the puncture 90. In a further alternative, a solid plug may be advanced into the puncture 90 adjacent or around the apparatus 2. Thus, the balloon 6 may provide hemostasis and/or prevent a plug or other solid component or liquid sealing compound 146 from entering the vessel 94 as it is introduced into the puncture 90.

Figure 9:
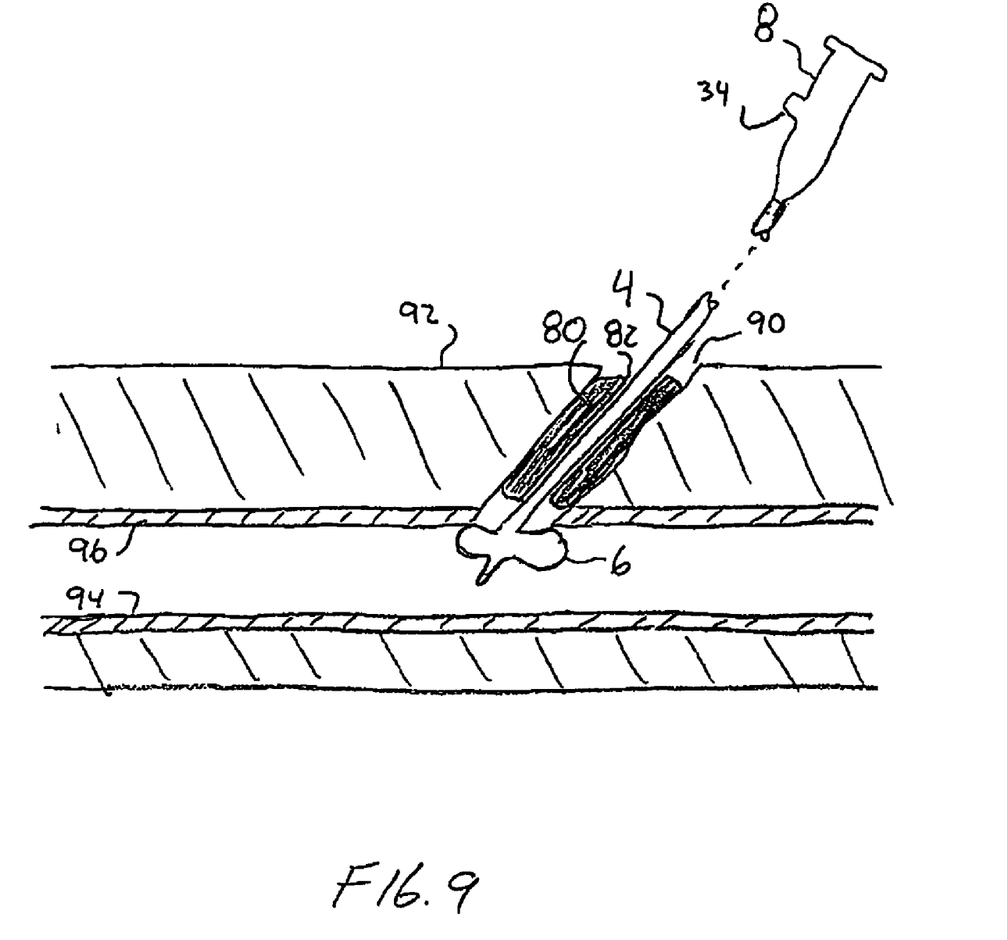
FIG. 9 is a cross-sectional view of a puncture extending through tissue to a body lumen, showing a method for sealing the puncture.

For example, FIG. 9 illustrates the apparatus 2 being used in connection with a plug or other carrier 80. The carrier 80 includes a lumen 82 therein sized to receive the elongate member 4 and expandable member 6 (in the contracted condition) therethrough. The carrier 80 may be formed from a lyophilized (i.e., freeze-dried) PEG polymer that contains hydrolytically degradable chemical groups, such as the plugs disclosed in co-pending application Ser. Nos. 10/982,387 and 10/982,384, both filed Nov. 5, 2004. The entire disclosures of these applications are expressly incorporated by reference herein.

Turning to FIG. 8F, once sufficient sealing compound 146 is delivered, the sealing compound 146 may given sufficient time to at least partially (or fully) solidify, e.g., between about five and one hundred eighty (5-180) seconds. The balloon 6 may then be collapsed to the contracted condition and then withdrawn from the puncture 90.

Figure 6:
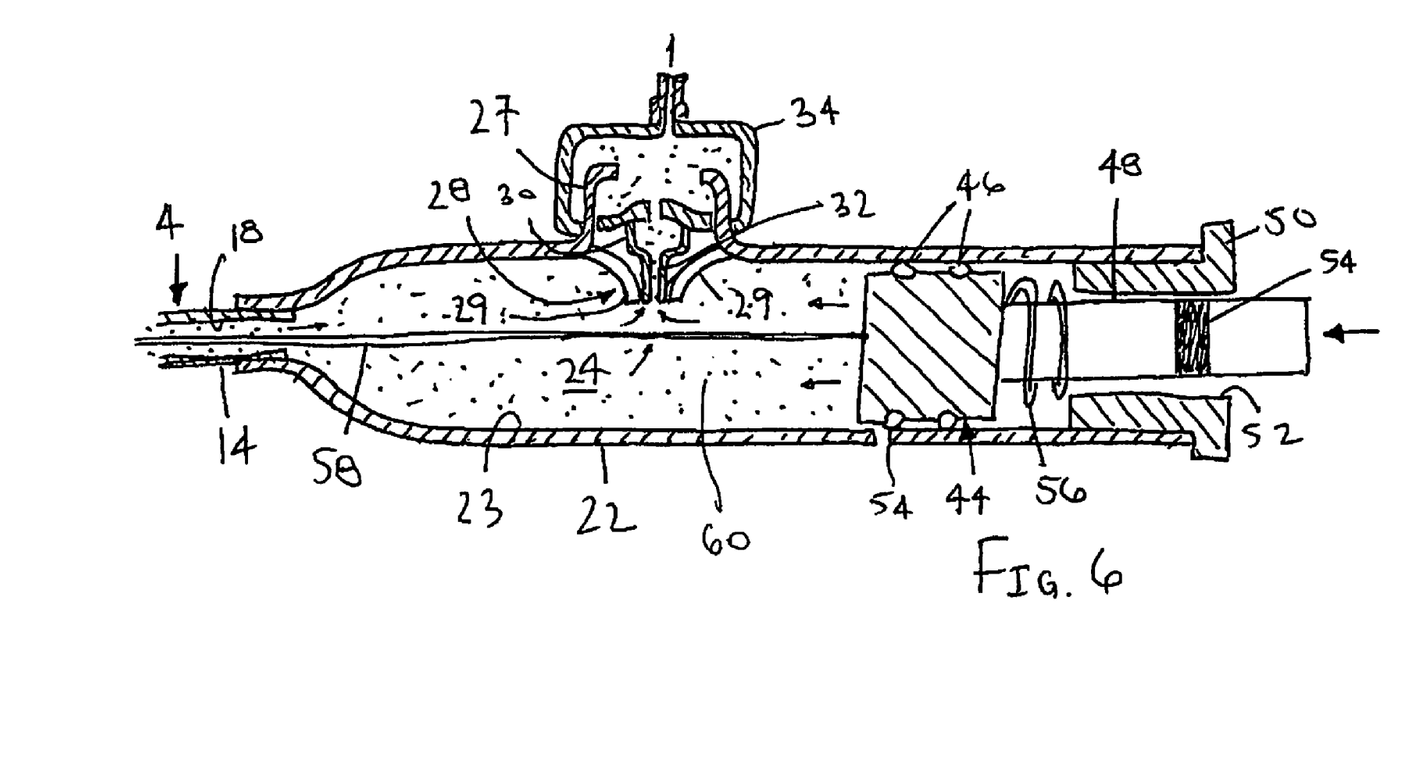
FIG. 6 is a cross-sectional side view of the hub of FIG. 2, showing an evacuation port communicating with an interior of the hub through the valve, allowing fluid to escape from the interior to prevent over-inflation of the balloon.

With reference to FIG. 6, a syringe 10 or other device (not shown) may be used to evacuate inflation media 60 from the balloon flow path to collapse the balloon 6. For example, the syringe 10 may be secured to the connector 42 on the end of the conduit 12, and the button 34 may be depressed to move the nipple 30 and fluid port 32 through the valve 28 into communication with the interior 24 of the housing 22. When the fluid port 32 is exposed to the interior 24 of the housing 22, a vacuum may be drawn on the syringe 10 by pulling plunger 11 to evacuate inflation media 60 from the interior 24, and therefore from the lumen 18 and interior 6c of the balloon 6 to deflate or otherwise collapse the balloon 6, as shown in FIG. 7. In addition, this vacuum may cause the piston 44 and pressure indicator 48 to retract into the hub subassembly 8 (i.e., move in the distal direction). In one embodiment, when the pressure indicator 48 is no longer visible (due to complete retraction inside the hub subassembly 8), the apparatus 2 may then be removed, knowing that the balloon 6 is sufficiently collapsed.

As the fluid is evacuated from the interior 24 of the housing 22, the bias of the piston 44 may cause the piston 44 to move distally, thereby lengthening the balloon 6 as it collapses. This may minimize the profile of the balloon 6 in the contracted condition, thereby facilitating removing the balloon 6 through the sealing compound 146 delivered into the puncture 90 without substantially disturbing the surrounding sealing compound 146.

To facilitate removing the balloon 6, a lubricious coating (not shown) may be provided on an exterior of the elongate member 4 and/or balloon 6, e.g., DOW 360 silicone fluid. Such a coating may prevent the sealing compound 146 from sticking to or otherwise pulling on the elongate member 4 and/or balloon 6 as the apparatus 2 is withdrawn.

Optionally, external pressure may be applied, e.g., by pressing manually against the skin 92 overlying the vessel 94, e.g., to at least partially suppress flow through the vessel 94. The balloon 6 (and the rest of the apparatus 2) may be removed, and the external pressure may be maintained for sufficient time to allow the sealing compound 146 to solidify further, e.g., between about ten and one hundred eighty (10-180) seconds. The sealing compound may expand, e.g., due to its elasticity and/or due to further solidification, thereby substantially sealing the relatively small tract remaining upon removing the apparatus 2.

Alternatively, a tensioner (not shown) may be used to maintain tension on the balloon 6 for a prolonged period of time with the balloon 6 providing temporary hemostasis to allow the hydrogel to cure fully in the puncture 90 before removing the apparatus 2.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

What is claimed:

1. An apparatus for providing hemostasis within a puncture extending through tissue, comprising:
   an elongate member comprising proximal and distal ends defining a longitudinal axis therebetween, and a lumen extending between the proximal and distal ends, the distal end having a size sufficient to be inserted into a relatively small puncture or body lumen and terminating in a substantially atraumatic tip;
   an expandable member carried on the distal end of the elongate member proximal to the atraumatic tip;
   a housing on the proximal end of the elongate member, the housing including an interior communicating with the lumen of the elongate member;
   a valve assembly comprising a one-way valve allowing access into the housing interior upon application of a pressure differential across the valve for delivering fluid into the housing interior to expand the expandable member, the one-way valve otherwise biased closed to provide a substantially fluid-tight seal that prevents fluid from escaping from the housing interior, the valve assembly further comprising a movable plunger that is insertable through the valve and an actuator coupled to the plunger for inserting the plunger through the valve for manually overriding and opening the valve to allow access into the housing interior;
   a piston slidable within the housing interior from a distal position to a proximal position as fluid is delivered through the valve into the housing interior; and
   a connecting member coupled to the piston and extending to a location distal to the expandable member, a distal end of the expandable member is directed proximally by the connecting member as the piston moves from the distal position to the proximal position for shortening the expandable member as the expandable member expands.

2. The apparatus of claim 1, further comprising:
   a pressure indicator coupled to the piston for providing feedback indicating that sufficient fluid has been delivered into the interior to expand the expandable member to a predetermined expanded condition.

3. The apparatus of claim 2, the pressure indicator comprising a visual indicator that is exposed from the housing when the expandable member is expanded to the predetermined expanded condition.

4. The apparatus of claim 2, wherein the piston is biased to the distal position.

5. The apparatus of claim 1, wherein the piston is biased to the distal position, thereby biasing the connecting member distally to subject the expandable member to axial tension and thereby minimize a profile of the expandable member in a contracted condition.

6. The apparatus of claim 2, further comprising an evacuation port in the housing that is substantially isolated from the housing interior when the piston is in the distal position, the evacuation port communicating with the housing interior when the piston is at or proximal of a predetermined proximal position to thereby prevent overexpansion of the expandable member.

7. The apparatus of claim 1, further comprising an actuator coupled to the plunger for moving the plunger between a first position, which does not override the valve, and a second position, which overrides and opens the valve, and in which a fluid port may be extended through the valve and in communication with the housing interior.

8. The apparatus of claim 7, the actuator being movable inwardly relative to the housing to move the plunger from the first position to the second position, the actuator being biased outwardly such that the plunger returns to the first position when the actuator is released relative to the housing.

9. The apparatus of claim 7, wherein the plunger is alternately securable in the first and second positions upon activating and deactivating the actuator.

10. The apparatus of claim 1, further comprising an elongate sheath comprising proximal and distal ends, and a lumen extending therebetween, the lumen sized for receiving the elongate member therethrough when the expandable member is in a contracted condition.

11. The apparatus of claim 10, further comprising a sealing compound deliverable through the elongate sheath around the elongate member.

12. An apparatus for providing hemostasis within a puncture extending through tissue, comprising:
    an elongate member comprising proximal and distal ends defining a longitudinal axis therebetween, and a lumen extending between the proximal and distal ends, the distal end having a size sufficient to be inserted into a relatively small puncture or body lumen;
    an expandable member carried on the distal end of the elongate member;
    a housing on the proximal end of the elongate member, the housing including an interior communicating with the lumen of the elongate member;
    a pressure indicator on the housing for providing feedback indicating that sufficient fluid has been delivered into the housing interior to expand the expandable member to a predetermined expanded condition, the pressure indicator comprising a piston slidable within the housing from a distal position to a proximal position, whereby a visual indicator on the piston projects from the housing and becomes visible when sufficient fluid has been delivered into the housing interior to expand the expandable member to the predetermined expanded condition;
    a pressure relief mechanism that automatically allows fluid to escape from the housing interior when a predetermined pressure is exceeded, the pressure relief mechanism comprising an evacuation port in the housing that is substantially isolated from the housing interior when the piston moves between the distal and proximal positions, the evacuation port communicating with the housing interior when the piston moves beyond the proximal position, thereby allowing fluid to escape from the housing interior; and
    a connecting member coupled to the piston and extending to a location distal to the expandable member, such that the connecting member is directed proximally as the piston moves from the distal position to the proximal position to direct a distal end of the expandable member proximally for shortening the expandable member as the expandable member expands.

13. The apparatus of claim 12, wherein the housing extends axially from the proximal end of the elongate member, wherein piston is slidable along the longitudinal axis within the housing between the distal and proximal positions, and wherein the valve assembly is provided on a side wall of the housing.

14. An apparatus for providing hemostasis within a puncture extending through tissue, comprising:

an elongate member comprising proximal and distal ends defining a longitudinal axis therebetween, and a lumen extending between the proximal and distal ends;

an expandable member carried on the distal end of the elongate member;

a housing on the proximal end of the elongate member, the housing including an interior communicating with the lumen of the elongate member;

a valve assembly comprising a one-way valve allowing access into the housing interior upon application of a pressure differential across the valve;

a pressure indicator comprising a piston slidable within the housing from a distal position to a proximal position, whereby a visual indicator on the piston projects from the housing and becomes visible when sufficient fluid has been delivered into the housing interior to expand the expandable member to a predetermined expanded condition;

a pressure relief mechanism comprising an evacuation port in the housing that is substantially isolated from the housing interior when the piston moves between the distal and proximal positions, the evacuation port communicating with the housing interior when the piston moves beyond the proximal position, thereby allowing fluid to escape from the housing interior when a predetermined pressure is exceeded; and a connecting member coupled to the piston and extending to a location distal to the expandable member, such that the connecting member is directed proximally as the piston moves from the distal position to the proximal position to direct a distal end of the expandable member proximally for shortening the expandable member as the expandable member expands.

15. The apparatus of claim 14, wherein the distal end has a size sufficient to be inserted into a relatively small puncture or body lumen.

16. The apparatus of claim 14, wherein the piston is biased to the distal position, thereby biasing the connecting member distally to subject the expandable member to axial tension and thereby minimize a profile of the expandable member in a contracted condition.

* * * * *